(12) United States Patent
Kim et al.

(10) Patent No.: US 9,974,493 B2
(45) Date of Patent: May 22, 2018

(54) APPARATUS AND METHOD FOR OBTAINING COMPUTED TOMOGRAPHY

(71) Applicants: Vatech Co., Ltd., Gyeonggi-do (KR); Vatech Ewoo Holdings Co., Ltd., Gyeonggi-do (KR)

(72) Inventors: Tae Woo Kim, Gyeonggi-do (KR); Hyung Keun Lim, Gyeonggi-do (KR); Jin Pyo Chun, Gyeonggi-do (KR); Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 121 days.

(21) Appl. No.: 14/915,307

(22) PCT Filed: Aug. 26, 2014

(86) PCT No.: PCT/KR2014/007946
§ 371 (c)(1),
(2) Date: Feb. 29, 2016

(87) PCT Pub. No.: WO2015/030472
PCT Pub. Date: Mar. 5, 2015

(65) Prior Publication Data
US 2016/0213336 A1    Jul. 28, 2016

(30) Foreign Application Priority Data

Aug. 27, 2013  (KR) .................. 10-2013-0101974
Aug. 27, 2013  (KR) .................. 10-2013-0102030

(51) Int. Cl.
*A61B 6/00*    (2006.01)
*A61B 6/03*    (2006.01)
(Continued)

(52) U.S. Cl.
CPC .............. *A61B 6/032* (2013.01); *A61B 6/027* (2013.01); *A61B 6/04* (2013.01); *A61B 6/14* (2013.01); *A61B 6/4441* (2013.01)

(58) Field of Classification Search
CPC .. A61B 6/032; A61B 6/04; A61B 6/14; A61B 6/027; A61B 6/4441
See application file for complete search history.

(56) References Cited

U.S. PATENT DOCUMENTS

| 6,435,714 B1 * | 8/2002 | Bruder ................... A61B 6/032 378/196 |
| 2007/0104309 A1 * | 5/2007 | Schonborn ........... A61B 6/4441 378/4 |

(Continued)

FOREIGN PATENT DOCUMENTS

| JP | 2006-263052 A | 10/2006 |
| JP | 2006-280844 A | 10/2006 |

(Continued)

*Primary Examiner* — Courtney Thomas
(74) *Attorney, Agent, or Firm* — IP Legal Services, LLC

(57) ABSTRACT

Apparatus and method for obtaining computed tomography are disclosed. The computed tomography apparatus includes: an X-ray sensor and an X-ray generator disposed on both sides of a subject and facing each other; a first driving unit configured to move at least one of the X-ray sensor and the X-ray generator reciprocally in an angle range; and a second driving unit moving configured to move at least one of the X-ray sensor and the X-ray generator in a vertical direction of the object, simultaneously or alternately with the first driving unit. The computed tomography method includes a first driving step to move reciprocally at least one of an X-ray sensor and an X-ray generator, disposed on both sides of a subject and facing each other, in a range of an angle; and a second driving step to move at least one of the X-ray sensor and the X-ray generator, simultaneously or alternately with the first driving step, to (Continued)

control the at least one of the X-ray sensor and the X-ray generator to move in a vertical direction of the subject.

13 Claims, 13 Drawing Sheets

(51) Int. Cl.
*A61B 6/04* (2006.01)
*A61B 6/14* (2006.01)
*A61B 6/02* (2006.01)

(56) References Cited

U.S. PATENT DOCUMENTS

| | | | |
|---|---|---|---|
| 2009/0080604 A1* | 3/2009 | Shores | A61B 6/032 378/37 |
| 2011/0176717 A1 | 7/2011 | Siren et al. | |
| 2012/0243762 A1 | 9/2012 | Kanerva et al. | |
| 2015/0250431 A1* | 9/2015 | Yorkston | A61B 6/548 378/12 |
| 2015/0305696 A1 | 10/2015 | Yamakawa et al. | |

FOREIGN PATENT DOCUMENTS

| | | |
|---|---|---|
| JP | 2012-196451 A | 10/2012 |
| WO | 2012/008492 A1 | 1/2012 |

\* cited by examiner

APPARATUS AND METHOD FOR OBTAINING COMPUTED TOMOGRAPHY

CROSS REFERENCE TO RELATED APPLICATIONS

This application is a National Stage Patent Application of PCT International Patent Application No. PCT/KR2014/007946 (filed on Aug. 26, 2014) under 35 U.S.C. § 371, which claims priority to Korean Patent Application Nos. 10-2013-0101974 (filed on Aug. 27, 2013) and 10-2013-0102030 (filed on Aug. 27, 2013), the teachings of which are incorporated herein in their entireties by reference.

TECHNICAL FIELD

The present invention relates to an X-ray tomography apparatus, i.e. a computed tomography (CT) apparatus, and a method for obtaining CT method. More particularly, the present invention relates to a dental CT apparatus, in which the head of a human body including teeth is a main target, and a CT method using the same.

BACKGROUND ART

In the medical industry, an X-ray apparatus refers to an apparatus that causes an amount of X-rays to pass through a part of a human body to obtain an image therefrom, receives X-rays that have passed through the body part using an X-ray sensor, and provides an image using electrical signals caused based on received X-rays. Since X-rays that have passed through the body part cause different electrical signals according to the X-ray absorption ratios of individual locations of the body part, an image can be produced by processing the electrical signals using a central processing unit of the X-ray apparatus.

In the dental industry, an X-ray computed tomography (CT) apparatus refers to an apparatus that produces a tomographic image or, as required, a three-dimensional (3D) image of a set of teeth, the jaw joint, or the head, which is a main part of concern of body parts of a patient, by obtaining X-ray images of the body part at a variety of angles while rotating around the entire portions of the body part and then reconstructing the obtained X-ray images.

In the dental X-ray CT apparatus of the related art, an X-ray generator is disposed on one side of a rotary arm, and an X-ray sensor is disposed on the other side of the rotary arm to face the an X-ray generator. Both the X-ray generator and the X-ray sensor are cased. As the rotary arm rotates about the fixed axis of rotation above the head of a patient, the X-ray generator and the X-ray sensor obtain a plurality of X-ray images while rotating around the dental arch of the patient. The X-ray images are obtained through rotation to an angle of about at least 200° according to image reconstruction schemes. After first image obtaining, in general, the X-ray sensor and the X-ray generator are rotated again in the direction of rotation during first image obtaining in order to move the X-ray sensor and the X-ray generator to the initial positions for second image obtaining.

In general, the X-ray sensor rotates with the smaller radius to the center of the head of the patient, and the X-ray generator rotates with the larger radius to the center of the head of the patient. When the CT apparatus is installed, a space for the maximum radius of rotation is required. Thus, the space which is greater than the actual size of the apparatus is necessary. In addition, in the case of high-speed scanning, the X-ray generator and the X-ray sensor rotating at high speed may cause the patient nervous and to make him/her move. The movement may lead to a motion artifact that degrades image quality.

DISCLOSURE

Technical Problem

Accordingly, the present invention is intended to propose a computed tomography (CT) apparatus and a CT method, able to reduce the ranges of rotation, i.e. the ranges of the angles of rotation, of an X-ray generator and an X-ray sensor during CT image obtaining, to be installed within a smaller space by employing an X-ray image scanning scheme according to the reduced ranges of rotation, and to reduce factors that may degrade image quality, such as a motion artifact.

Technical Solution

In order to achieve the above object, according to one aspect of the present invention, a computed tomography (CT) apparatus may include: an X-ray sensor and an X-ray generator disposed on both sides of a subject and facing each other; a first driving unit configured to move reciprocally at least one of the X-ray sensor and the X-ray generator in an angle range; and a second driving unit configured to move at least one of the X-ray sensor and the X-ray generator in a vertical direction of an object, simultaneously or alternately with the first driving unit.

The second driving unit may move at least one of the X-ray sensor and the X-ray generator, simultaneously with an operation of the first driving unit, to form a Z-shaped path, or may move at least one of the X-ray sensor and the X-ray generator, alternately with the operation of the first driving unit, to form a vertically-mirrored S-shaped path.

The angle may range from 30° to 180°, and the reciprocal movement may be a rectilinear or rotational movement.

The CT apparatus may further include an integrated case. The integrated case includes: first and second areas covering the X-ray sensor and the X-ray generator such that at least one of X-ray sensor and the X-ray generator is movable; and a third area connecting the first and second areas.

According to another aspect of the present invention, a CT apparatus may include: an X-ray sensor and an X-ray generator disposed on both sides of a subject and facing each other, wherein the X-ray sensor and the X-ray generator are configured move along first and second tracks in ranges of first and second angles about an axis of rotation between the X-ray sensor and the X-ray generator; and an integrated case providing a first area covering the X-ray sensor and the first track and a second area covering the X-ray generator and the second track. One of the first and second angles is 0° or ranges from 30° to 180°, and the other one of the first and second angles ranges from 30° to 180°.

The CT apparatus may further include a rotary arm, the X-ray sensor and the X-ray generator being connected to both ends thereof. The integrated case further includes a ceiling area connecting the first area and the second area and covering the rotary arm.

The integrated case may further include at least one third area connecting adjacent both ends of the first and second areas.

The distances of the first track and the second track to the subject may be equal or different.

At least one of the first and second tracks may move upwards and downwards in a vertical direction of the subject within the integrated case.

According to a further aspect of the present invention, a CT method may include: a first driving step to move at least one of an X-ray sensor and an X-ray generator, disposed on both sides of a subject and facing each other, reciprocally in an angle range; and a second driving step of to move at least one of the X-ray sensor and the X-ray generator, simultaneously or alternately with the first driving step, in a vertical direction of the subject.

In the second driving step, at least one of the X-ray sensor and the X-ray generator, may move simultaneously with the first driving step, to form a Z-shaped path, or alternately with the first driving step, to form a vertically-mirrored S-shaped path.

The angle in the first driving step may range from 30° to 180°, and the reciprocal movement may be a rectilinear or rotational movement.

Advantageous Effects

According to the present invention having the above-described characteristics, the apparatus and the CT method can reduce the ranges of rotation, i.e. the ranges of the angles of rotation, of the X-ray generator and the X-ray sensor during CT image obtaining, can be disposed within a smaller space by employing an X-ray image scanning scheme according to the reduced ranges of rotation, and can reduce factors that may degrade image quality, such as a motion artifact, by covering the rotation of the X-ray sensor and/or the X-ray generator from the outside.

MODE FOR INVENTION

Figure 1:
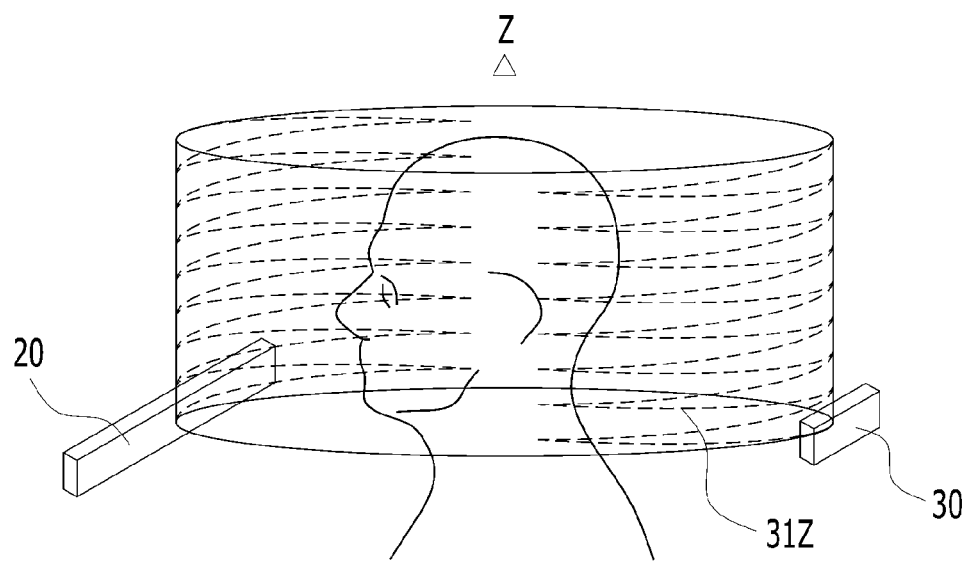
FIG. 1 schematically illustrates a CT method according to an embodiment of the present invention.

Reference will now be made in detail to various embodiments of the present invention, specific examples of which are illustrated in the accompanying drawings. The embodiments set forth herein are provided for illustrative purposes to fully convey the concept of the present invention. It will be apparent to a person skilled in the art that the present invention should not be construed to be limited to these embodiments and may be embodied in many different forms within the scope of the invention. Throughout the drawings, the same reference numerals will refer to the same or like parts. Descriptions of some components depicted in a specific drawing will be omitted, when their reference numerals are identical to those of the components described with reference to another drawing.

FIG. 1 schematically illustrates a CT method according to an embodiment of the present invention.

As illustrated in the drawing, an X-ray sensor 20 and an X-ray generator 30 are disposed on opposite sides, i.e. are disposed to face each other, to locate a subject between them. At least one of the X-ray sensor 20 and the X-ray generator 30 scans the subject while moving along zigzag paths 31Z, using a first driving unit and a second driving unit. The first driving unit controls the X-ray sensor 20 and the X-ray generator 30 to reciprocally move within the ranges of predetermined angles on both sides of the subject while facing each other. The second driving unit controls to move at least one of the X-ray sensor 20 and the X-ray generator 30 in the vertical direction of the subject.

For reference, it is illustrated in the Figure that the X-ray sensor 20 and the X-ray generator 30 are rotated about the axis of rotation therebetween by the first driving unit while being moved in the vertical direction of the subject, i.e. the direction of the axis of rotation, by the second driving unit, such that the X-ray sensor 20 and the X-ray generator 30 scan the subject while moving along the zigzag paths 31Z.

However, unlike the drawings, the first driving unit may reciprocally drive to move one of the X-ray sensor 20 and the X-ray generator 30 in the ranges of angles, and the second driving unit may drive to move one of the X-ray sensor 20 and the X-ray generator 30 in the vertical direction of the subject, such that one of the X-ray sensor 20 and the X-ray generator 30 scans the subject while moving along the zigzag paths 31Z. The reciprocal movement driven by the first driving unit may be a rectilinear movement in the ranges of angles.

Hereinafter, for the sake of brevity, reference will be described the most complex example among CT methods according to the present invention, i.e. a case in which the first driving unit reciprocally rotates the X-ray sensor 20 and the X-ray generator 30 in the ranges of predetermined angles, and the second driving unit moves the X-ray sensor 20 and the X-ray generator 30 in the direction of the axis of ordinates. The other examples will be apparent to a skilled in the art from the following description.

Like a panoramic imaging sensor of a dental X-ray imaging apparatus, the X-ray sensor 20 may be disposed perpendicularly with respect to in the vertical direction of the subject by rotating a bar-shaped sensor from an angle in which the panoramic imaging sensor is oriented to 90° while obtaining panoramic images. Alternatively, the X-ray sensor may be a large-area sensor corresponding to an X-ray generator generating cone beams. Sensors having a variety of aspect ratios that are able to acquire data regarding multi-slice X-ray images as from MDCT as well as data regarding single-slide X-ray images may be employed. The X-ray sensor 20 may have the shape of an arc facing toward the subject, as required. The X-ray generator 30 is an X-ray radiation source, which emits X-ray beams collimated according to the shape of the corresponding X-ray sensor 20.

The first driving unit may be configured to rotate a structure connected to the X-ray sensor 20 and the X-ray generator 30, for example, a structure such as a rotary arm of the dental X-ray imaging apparatus, about the vertical axis of the subject. The driving unit may be configured to respectively move the X-ray sensor 20 and the X-ray generator while maintaining the X-ray sensor 20 and the X-ray generator 30 in the positional relationship of facing each other. The second driving unit may be configured to move, for example, the rotary arm of the dental X-ray imaging apparatus in the vertical direction of the subject, or may be configured to move a structure guiding the track of each of the X-ray sensor 20 and the X-ray generator 30, in the vertical direction of the subject. Detailed examples of the configurations thereof will be described later, and the configurations may be realized in various manners including the disclosed examples.

Solid lines on the figure indicate the tracks 31Z with respect to the position of the X-ray generator 30, and dotted lines on the figure indicate the tracks with respect to the position of the X-ray sensor 20.

The ranges of angles may be predefined depending on the reconstruction scheme of a CT image and the characteristics of an apparatus processing the CT image, or may be adjusted depending on the purpose of obtaining a CT image within the range of a predetermined maximum value or the characteristics of a subject.

Figure 2:
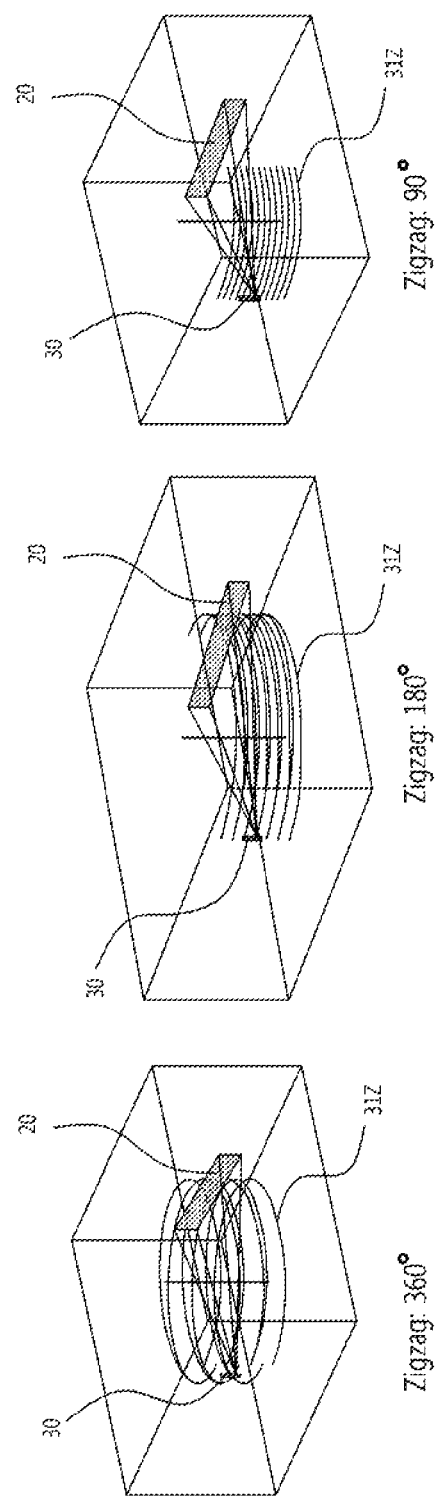
FIG. 2 schematically illustrates an exemplary embodiment of the CT method illustrated in FIG. 1, in which a variety of angle ranges are applied.

FIG. 2 schematically illustrates an exemplary embodiment of the CT method illustrated in FIG. 1, in which a variety of ranges of angles are applied. The tracks 31Z in FIG. 2 are with respect to the position of the X-ray generator 30. The zigzag paths 31Z may be formed in the angle range of 360°, 180°, 90°, or any angle therebetween, depending on the ranges of angles of partial rotation by the above-described first driving unit.

The zigzag paths 31Z illustrated in FIGS. 1 and 2 correspond to the case in which the first driving unit and the second driving unit simultaneously operate. The tracks 31Z are bended in the form of a letter "Z" in portions in which partial rotation is redirected. Alternatively, when the first driving unit and the second driving unit alternately operate, the tracks may be bent in the form of a Korean letter "ㄹ", i.e. the vertically-mirrored form of a letter "S", in portions in which partial rotation is redirected.

Figure 3:
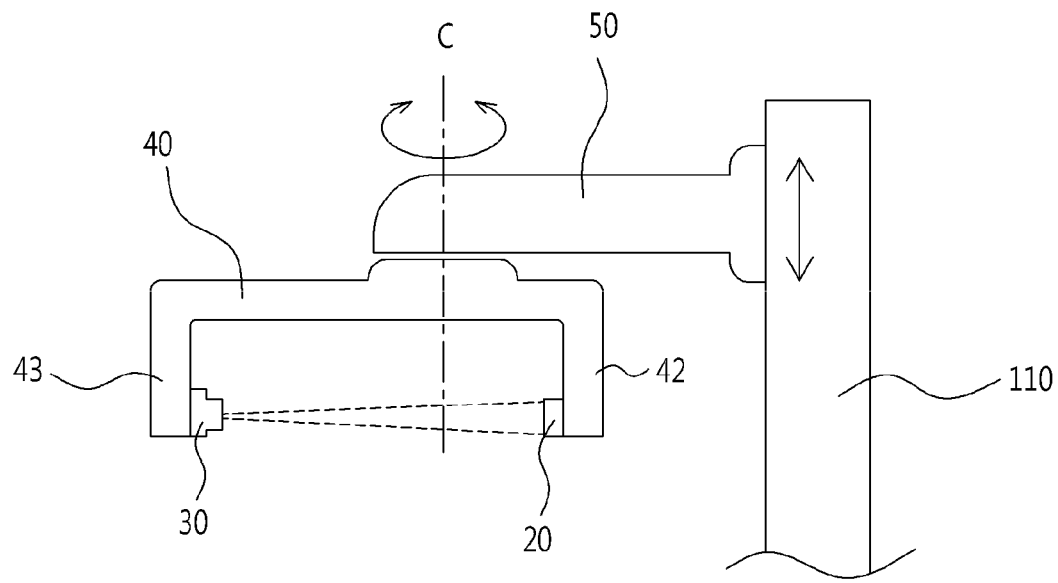
FIG. 3 illustrates an exemplary dental CT apparatus to which the CT method according to the present invention is applied.

FIG. 3 illustrates an exemplary dental CT apparatus to which the CT method according to the present invention is applied. In the dental CT apparatus, the X-ray generator 30 is mounted on one side of a rotary arm 40, and the X-ray sensor 20 is mounted on the other side of the rotary arm 40, facing the X-ray generator 30. As the rotary arm 40 rotates above the head of the patient, the X-ray generator 30 and the X-ray sensor 20 connected to the rotary arm 40 obtains a plurality of X-ray images while rotating around the head or the dental arch of the patient. The rotary arm 40 is connected to a prop 110 acting as a column of the apparatus by means of a rotary arm support 50. The rotary arm support 50 is connected to the prop 110 by means of a rotary arm lift controlling the rotary arm support 50 to move in the vertical direction with respect to the prop 110, such that the rotary arm 40 can be moved in the vertical direction of the subject (C), i.e. the axis of rotation thereof.

In the CT apparatus according to the present invention, a rotary driving unit corresponding to the above-described first driving unit is disposed between the rotary arm support 50 and the rotary arm 40 to partially rotate the rotary arm 40 to reciprocate in the range of a predetermined angle. A rotary arm lift corresponding to the above-described second driving unit moves the rotary arm support 50 and the rotary arm 40 in the vertical direction of the subject (C), in concert with the operation of the rotary driving unit. Consequently, the CT apparatus can scan a subject along a zigzag track.

The operation of the rotary driving unit and the operation of the rotary lift may be carried out simultaneously or may be carried out alternately in such a manner that the rotary arm lift operates at a point in time in which the partial rotation of the rotary driving unit is redirected. These operations are controlled by a driving controller disposed within the dental CT apparatus.

Figure 4:
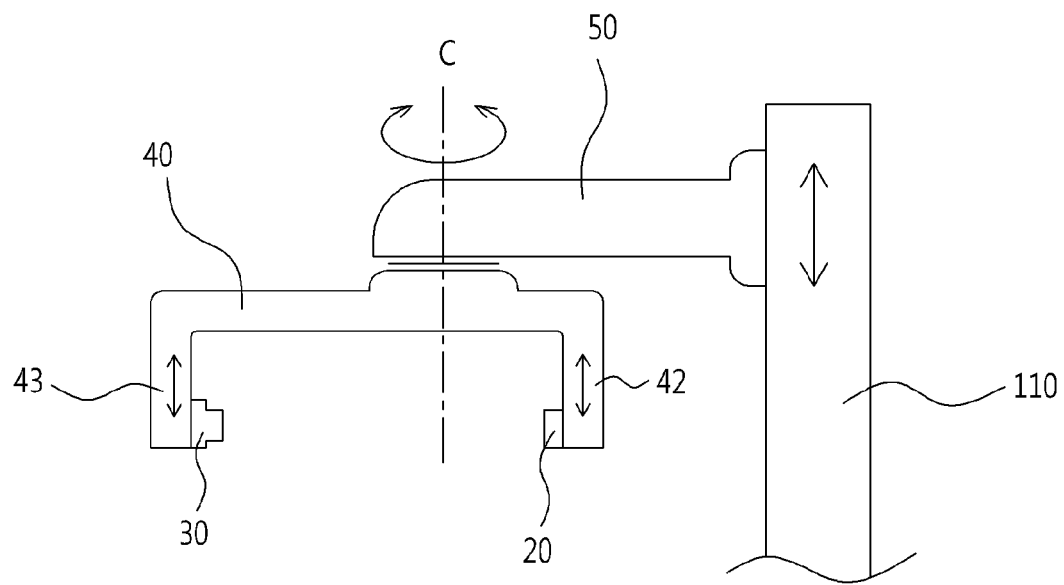
FIG. 4 illustrates an exemplary dental CT apparatus to which the CT method according to the present invention is applied.

FIG. 4 illustrates an exemplary dental CT apparatus to which the CT method according to the present invention is applied. In another embodiment of the dental CT apparatus, the above-described second driving unit may include a sensor lift disposed on a sensor-side vertical portion 42 of the rotary arm 40 and a generator lift disposed on a generator-side vertical portion of the rotary arm 40. The sensor lift and the generator lift are controlled in concert with each other to maintain the positions of the X-ray sensor 20 and the X-ray generator 30 facing each other. In addition, the rotary driving unit partially rotating the rotary arm 40 in the range of a predetermined angle, the sensor lift, and the generator lift are controlled to operate simultaneously or alternately such that the X-ray sensor 20 and the X-ray generator 30 scan the subject along the above-described zigzag paths.

Figure 5:
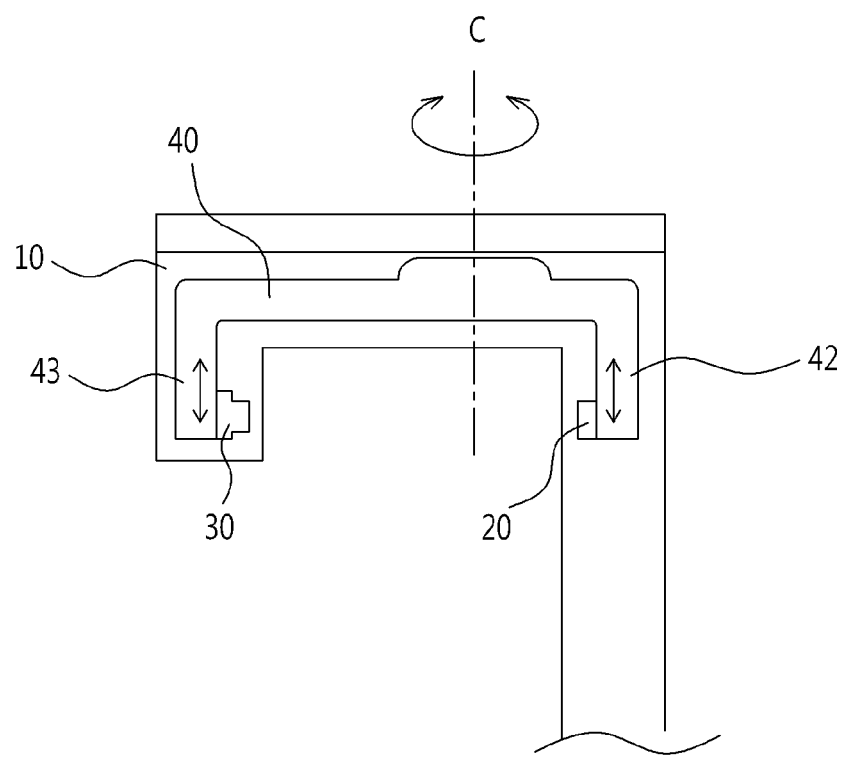
FIG. 5 illustrates an exemplary dental CT apparatus having an integrated case structure to which the CT method according to the present invention is applied.

FIG. 5 illustrates an exemplary dental CT apparatus having an integrated case structure to which the CT method according to the present invention is applied. In the present embodiment, the above-described first driving unit may be configured such that the first driving unit is disposed within an integrated case 10 and is connected to the rotary arm 40, and the second driving unit is configured the same as that of the foregoing embodiment described with reference to FIG. 4. The integrated case 10 may be formed according to the range of movement of the X-ray sensor 20 and the X-ray generator 30. For example, as in the present embodiment, when one of the X-ray sensor 20 and the X-ray generator 30 partially rotates along the track closer to the vertical axis of the subject (C) and the other one of the X-ray sensor 20 and the X-ray generator 30 partially rotates along the farther track, the size of the integrated case 10 may be determined such that the integrated case 10 can cover the tracks of the X-ray sensor 20 and the X-ray generator 30, thereby reducing the space in which the apparatus is disposed.

Although not illustrated in a separate drawing, in the embodiment illustrated in FIG. 3, the subject may be positioned between the X-ray sensor 20 and the X-ray generator 30, and an integrated case covering the rotary arm support 50 and the rotary arm 40 in addition to the X-ray sensor 20 and the X-ray generator 30 may be used. In this case, the rotary arm support 50 and the rotary arm 40 can move upwards and downwards and rotate within the integrated case, such that the X-ray sensor 20 and the X-ray generator 30 can scan the subject along the zigzag paths.

Configurations of the dental CT apparatus including the above-described integrated case 10 will be described later with reference to several embodiments.

Figure 6:
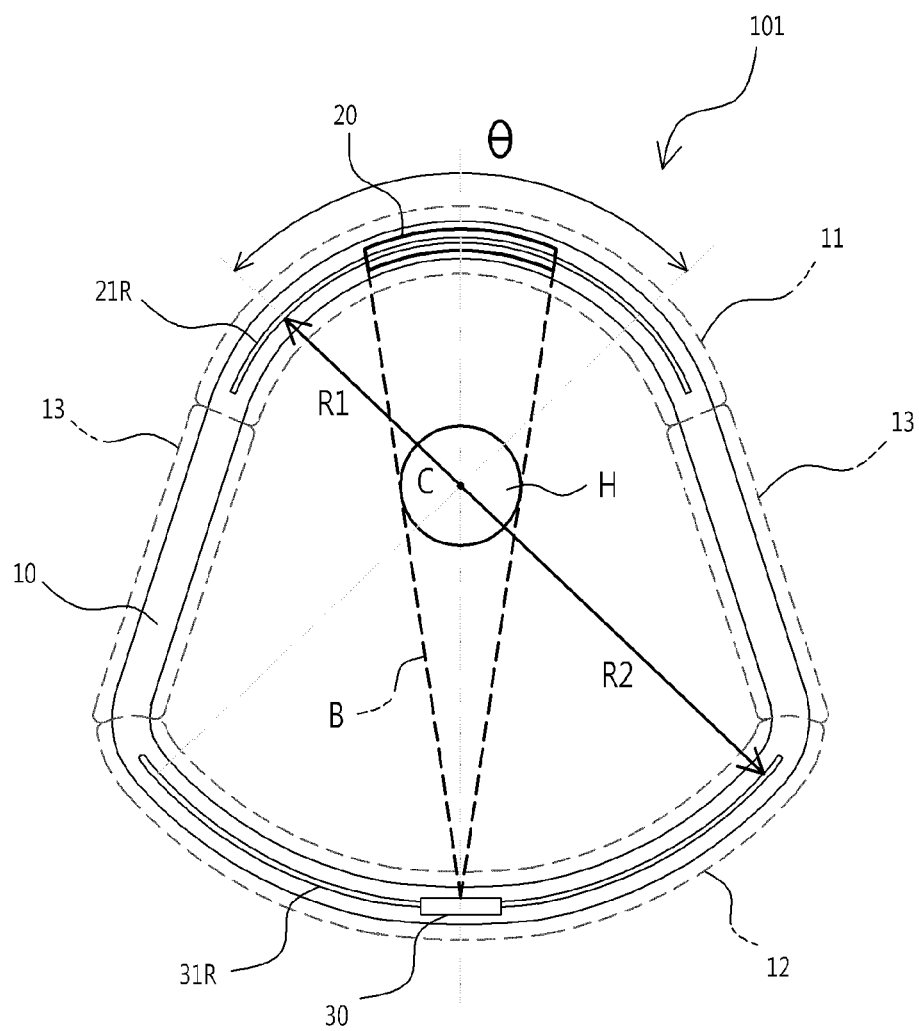
FIG. 6 illustrates an image obtaining track of a CT apparatus according to an embodiment of the present invention.

FIG. 6 illustrates an image obtaining track of a CT apparatus according to an embodiment of the present invention.

The CT apparatus 101 according to the present embodiment includes the X-ray sensor 20 and the X-ray generator 30 disposed on both sides of a subject H and facing each other. The X-ray sensor 20 and the X-ray generator 30 can move along first and second tracks in the ranges of a first angle and a second angle about a rotary axis therebetween. In particular, one of the first and second angle ranges is from 0° or 30° to 180°, and the other one is from 30° to 180°.

Specifically, the CT apparatus 101 according to the present invention may be configured such that at least one of the X-ray sensor 20 and the X-ray generator 30 moves at an angle ranging from 30° to 180° while the other one of the X-ray sensor 20 and the X-ray generator 30 is fixed (with the range of the angle being set to 0°), or that both the X-ray sensor 20 and the X-ray generator 30 are movable in the angle range from 30° to 180°. In addition, the movement of the X-ray sensor 20 and/or the X-ray generator 30 may be a rectilinear movement or a rotational movement.

Hereinafter, reference will be made to the most complex embodiment of the CT apparatus according to the present invention, i.e. the case in which both the X-ray sensor 20 and the X-ray generator 30 rotate in the angle range from 30° to 180°, for the sake of brevity. The other embodiments will be apparent to a person skilled in the art from the following description. For reference, the ranges of angles mentioned in the following description indicate the ranges of physical movement of the X-ray sensor and the X-ray generator about the axis of rotation between the X-ray sensor and the X-ray generator. The physical movements of the X-ray sensor and the X-ray generator are distinguished from the X-ray sensor or the X-ray generator rotating in position about an axis passing therethrough without a physical movement. The latter case will be apparent without detailed descriptions to a person skilled in the art.

The X-ray sensor 20 is movably mounted such that it can move while being guided by a first track 21R formed along a first track at an angle θ range from 30° to 180° about the subject H. The X-ray generator 30 is mounted such that X-ray generator 30 moves while being guided by a second track 31R formed along a second track. The distance R2 of the second track to the subject H is different from the distance R1 of the first track to the subject H. More specifically, the distance R2 of the second track to the subject H is greater than the distance R1 of the first track to the subject H.

In addition, the CT apparatus 101 according to the present embodiment includes the integrated case 10 that covers both the inside of the tracks facing the subject and the outside of the tracks facing away from the subject, such that the movement of the X-ray sensor 20 and the X-ray generator 30 along the tracks is not seen by the patient. In this regard, the integrated case 10 includes a first area 11 covering the first track 21R and the X-ray sensor 20 and a second area 12 covering the second track 31R and the X-ray generator 30. The first area 11 and the second area 12 are connected to each other via third areas 13 formed along extensions of the first and second tracks, such that the integrated case 10 has the shape of a rim defined by connecting two arcs having different radii. An alternative embodiment may provide an open shape in which at least a portion of the rim corresponding to the third areas 13 is omitted. A variety of other embodiments are possible. A variety of embodiments of the integrated case 10 will be described later.

The X-ray generator 30 may be a generator that radiates a cone beam or a fan beam depending on the CT method. The X-ray sensor 20 may have a suitable aspect ratio depending on the shape of an X-ray beam B. Although not illustrated in the drawing, the first track 21R and second track 31R may be formed to be movable upwards and downwards in the direction perpendicular to the plane of the drawing within a predetermined range. For example, when the subject H is the head of the patient, the range of the upward-downward movement is from the top to the bottom of the head of the patient. The height of the integrated case may be set to cover the range of the upward-downward movement.

As illustrated in the drawing, the distances from the subject H to the outer circumferences of the first area 11 and the second area 12 of the integrated case 10 are different. More specifically, the ranges of movement of the X-ray sensor 20 and the X-ray generator 30 are limited to an angle θ equal to or greater than 90° and less than 180°. When the radius of the operation from the subject H is shorter, the case may be formed to be close to the subject. When the radius of the operation from the subject H is greater, the case may be formed according to the radius. It is thereby possible to reduce the overall space in which the apparatus is disposed.

Describing the operation of the CT apparatus 101 according to the present embodiment, in the case in which the X-ray generator 30 and the X-ray sensor 20 maintain the relative positions of facing each other on both sides of the subject H, the center axis of the X-ray beam B is rotated (partially rotated) in the range of the angle θ about the center C of the subject H, which acts as the axis of rotation, such that X-ray transmission data are obtained at a variety of angles. The X-ray transmission data obtained in this manner are reconstructed, thereby forming a tomographic image of at least one single layer or a three-dimensional (3D) image in which a plurality of tomographic images are reconstructed. Here, the X-ray beam B may be partially rotated once to the angle θ about the subject H. This process may be repeated several times. Together with this process being repeated several times, the upward-downward movement of the first track 21R and the second track 31R may be carried out.

The present embodiment and the following embodiments are described, by way of example, with respect to a case in which the radius of curvature R1 of the first area 11 of the integrated case 10 is smaller than the radius of curvature R2 of the second area 12. Although this arrangement is commonly used because it is advantageous that the X-ray sensor 20 is closer to the subject H than the X-ray generator 30 to obtain a clearer image, the distances may be changed as required. In addition, the radius of curvature R1 of the first area 11 and the radius of curvature R2 of the second area 12 of the integrated case 10 may be the same if it is necessary.

Figure 7:
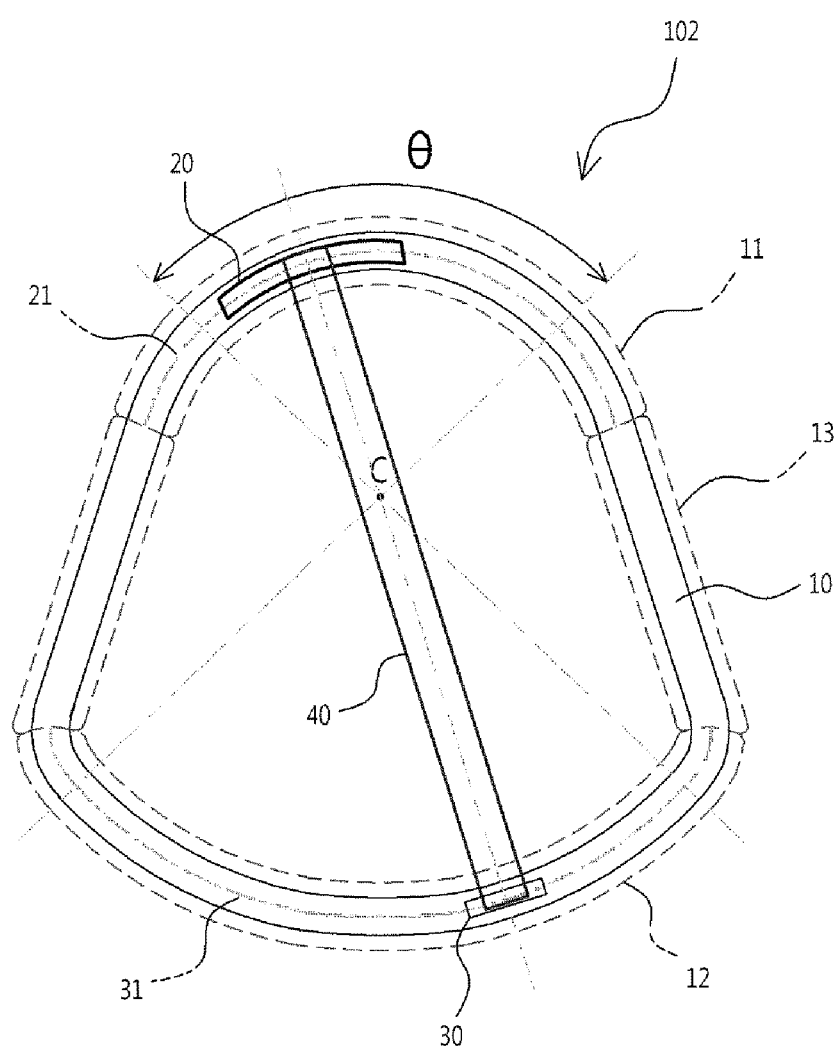
FIG. 7 illustrates an image obtaining track of a CT apparatus according to an embodiment of the present invention.

FIG. 7 illustrates an image obtaining track of a CT apparatus according to an embodiment of the present invention. In the CT apparatus according to the present embodiment 102, the X-ray sensor 20 and the X-ray generator 30 are the same as those described in the foregoing embodiment with reference to FIG. 1, and for the partial rotation of the X-ray sensor 20 and the X-ray generator 30, the rotary arm 40 having both ends connected to the X-ray sensor 20 and the X-ray generator 30 is provided in place of the tracks. The rotary arm 40 is configured to be partially rotatable to an angle θ about the center C of the subject, which acts as the axis of rotation. The rotary arm 40 can be disposed within a ceiling area connected to the first area 11 and the second area 12 of the integrated case 10. With the operation of the rotary arm 40, the X-ray sensor 20 moves along a first track 21, and the X-ray generator 30 moves along a second track 31. When the rotary arm 40 is disposed such that the movement thereof is not seen by the patient or the subject H, it is advantageous to prevent a motion artifact that would otherwise be caused by a movement of the patient. Alternatively, the rotary arm may be disposed to be concealed since it rotates above the head of the patient.

Since the first area 11 and the second area 12 in the integrated case 10 are connected via the ceiling area, the third areas 13 connecting the first area 11 and the second area 12 to the first track 21 and the second track 31 may be omitted. A shape due to the omission will be described later.

Figure 8:
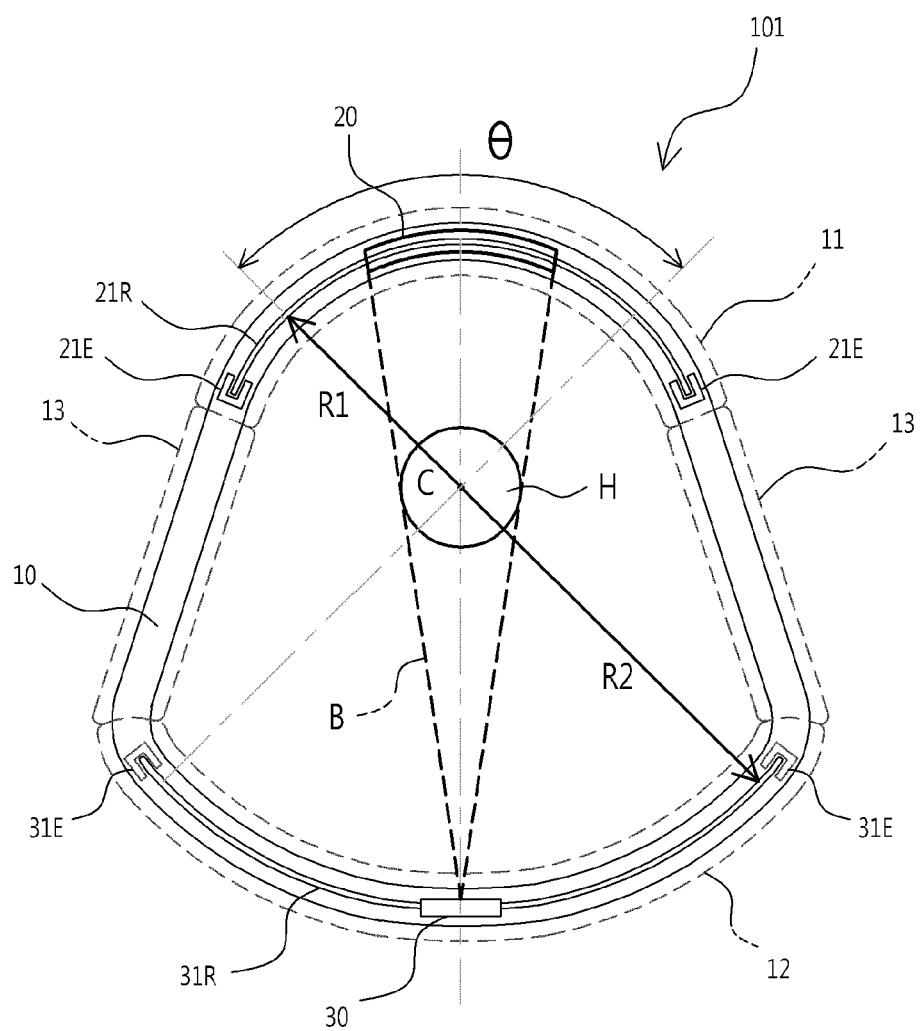
FIG. 8 illustrates an exemplary dental CT apparatus having an integrated case structure to which the CT method according to the present invention is applied.

FIG. 8 illustrates an exemplary dental CT apparatus having an integrated case structure to which the CT method according to the present invention is applied.

The CT apparatus 101 according to the present embodiment includes the X-ray sensor 20 and the X-ray generator 30 disposed on both sides of a subject H and facing each other. The X-ray sensor 20 is movably mounted by being guided by a first track 21R formed along a first track at an angle θ equal to or greater than 30° and less than 180° about the subject H. The X-ray generator 30 is mounted such that X-ray generator 30 moves while being guided by a second track 31R formed along a second track. The distance R2 of the second track to the subject H is different from the distance R1 of the first track to the subject H. More specifically, the distance R2 of the second track to the subject H is greater than the distance R1 of the first track to the subject H. In other words, the above-described first driving unit includes the first track 21R, the second track 31R, and a driving device moving the X-ray sensor 20 and the X-ray generator 30 along these tracks. Even in this case, the X-ray sensor 20 and the X-ray generator 30 are controlled to move while maintaining the positional relationship of facing each other.

In addition, the CT apparatus 101 according to the present embodiment includes the integrated case 10 that covers both the inside of the tracks facing the subject and the outside of the tracks facing away from the subject, such that the movement of the X-ray sensor 20 and the X-ray generator 30 along the tracks is not seen by the patient. In this regard, the integrated case 10 includes the first area 11 covering the first track 21R and the X-ray sensor 20 and the second area 12 covering the second track 31R and the X-ray generator 30. The first area 11 and the second area 12 are connected to each other via third areas 13 formed along extensions of the first and second tracks, such that the integrated case 10 has the shape of a rim defined by connecting two arcs having different radii. An alternative embodiment may provide an open shape in which at least a portion of the rim corresponding to the third areas 13 is omitted. A variety of other embodiments are possible. It is preferable that the integrated case 10 is formed of a material having a high level of X-ray transmittance in order to reduce influences to X-ray images. Although not clearly illustrated in the drawing, the first area 11 and the second area 12 of the integrated case 10 ensure that the X-ray sensor 20 and the X-ray generator 30 move in the vertical direction.

The X-ray generator 30 may be a generator that radiates a cone beam or a fan beam depending on the CT method. The X-ray sensor 20 may have a suitable aspect ratio depending on the shape of an X-ray beam B. As components corresponding to the above-described second driving unit, a first track lift 21E is provided on the first track 21R, and a second track lift 31E is provided on the second track 31R. With this configuration, the two tracks can move upwards and downwards in concert with each other in the direction perpendicular to the plane of the drawing, i.e. in the vertical direction of the subject C, within a predetermined range. For example, when the subject H is the head of the patient, the range of the upward-downward movement is from the top to the bottom of the head of the patient. The height of the integrated case may be set to cover the range of upward-downward movement.

As illustrated in the drawing, the distances from the subject H to the outer circumferences of the first area 11 and the second area 12 of the integrated case 10 are different. More specifically, the ranges of movement of the X-ray sensor 20 and the X-ray generator 30 are limited to an angle θ equal to or greater than 30° and less than 180°. When the radius of the operation from the subject H is shorter, the case may be formed to be close to the subject. When the radius of the operation from the subject H is greater, the case may be formed according to the radius. It is thereby possible to reduce the overall space in which the apparatus is disposed.

Describing the operation of the CT apparatus 101 according to the present embodiment, in the case in which the X-ray generator 30 and the X-ray sensor 20 maintain the relative positions of facing each other on both sides of the subject H, the center axis of the X-ray beam B is rotated (partially rotated) in the range of the angle θ about the center C of the subject H, which acts as the axis of rotation, such that X-ray transmission data are obtained at a variety of angles. The X-ray transmission data are obtained by changing the heights of the X-ray sensor 20 and the X-ray generator 30 with respect to the subject H currently or alternately with the partial rotation. The X-ray transmission data obtained in this manner are reconstructed, thereby forming a plurality of tomographic images and a 3D image in which the plurality of tomographic images are reconstructed. Here, simultaneously with the process of partially rotating the X-ray beam B to the angle θ about the subject H being repeated several times, the upward-downward movement of the first track 21R and the second track 31R may be carried out, such that zigzag paths are formed.

The present embodiment and the following embodiments are described, by way of example, with respect to a case in which the radius of curvature R1 of the first area 11 of the integrated case 10 is smaller than the radius of curvature R2 of the second area 12. Although this arrangement is commonly used because it is advantageous that the X-ray sensor 20 is closer to the subject H than the X-ray generator 30 is to obtain a clearer image, the distances may be changed as required. In addition, the radius of curvature R1 of the first area 11 and the radius of curvature R2 of the second area 12 of the integrated case 10 may be the same for some purposes.

Figure 9:
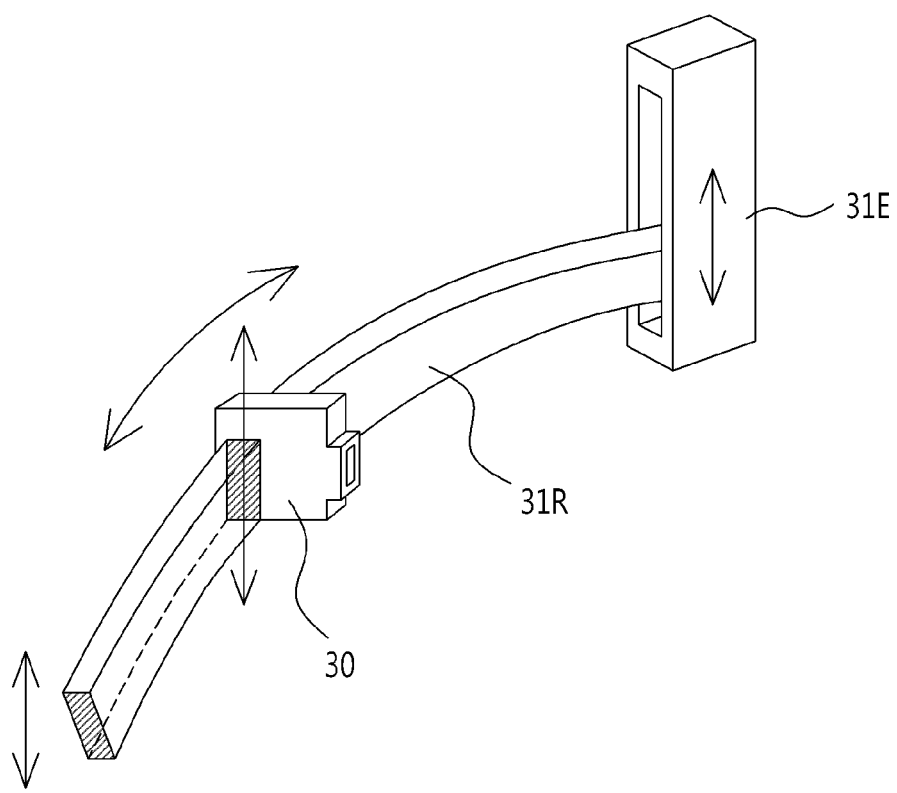
FIG. 9 more specifically illustrates the configurations of the track and the track lift in the embodiment illustrated in FIG. 8.

FIG. 9 more specifically illustrates the configurations of the track and the track lift in the embodiment illustrated in FIG. 8. FIG. 9 illustrates an example including the second track 31R to guide the X-ray generator 30 and the second track lift 31E to move upwards and downwards the second track 31R in a direction substantially perpendicular thereto. The second track lift 31E may be disposed on either end of the second track 31R or in a third position that does not interfere with the movement of the X-ray generator 30 along the direction of the track. This exemplary configuration may be applied to the first track 21R and the X-ray sensor 20 as described above.

Figure 10:
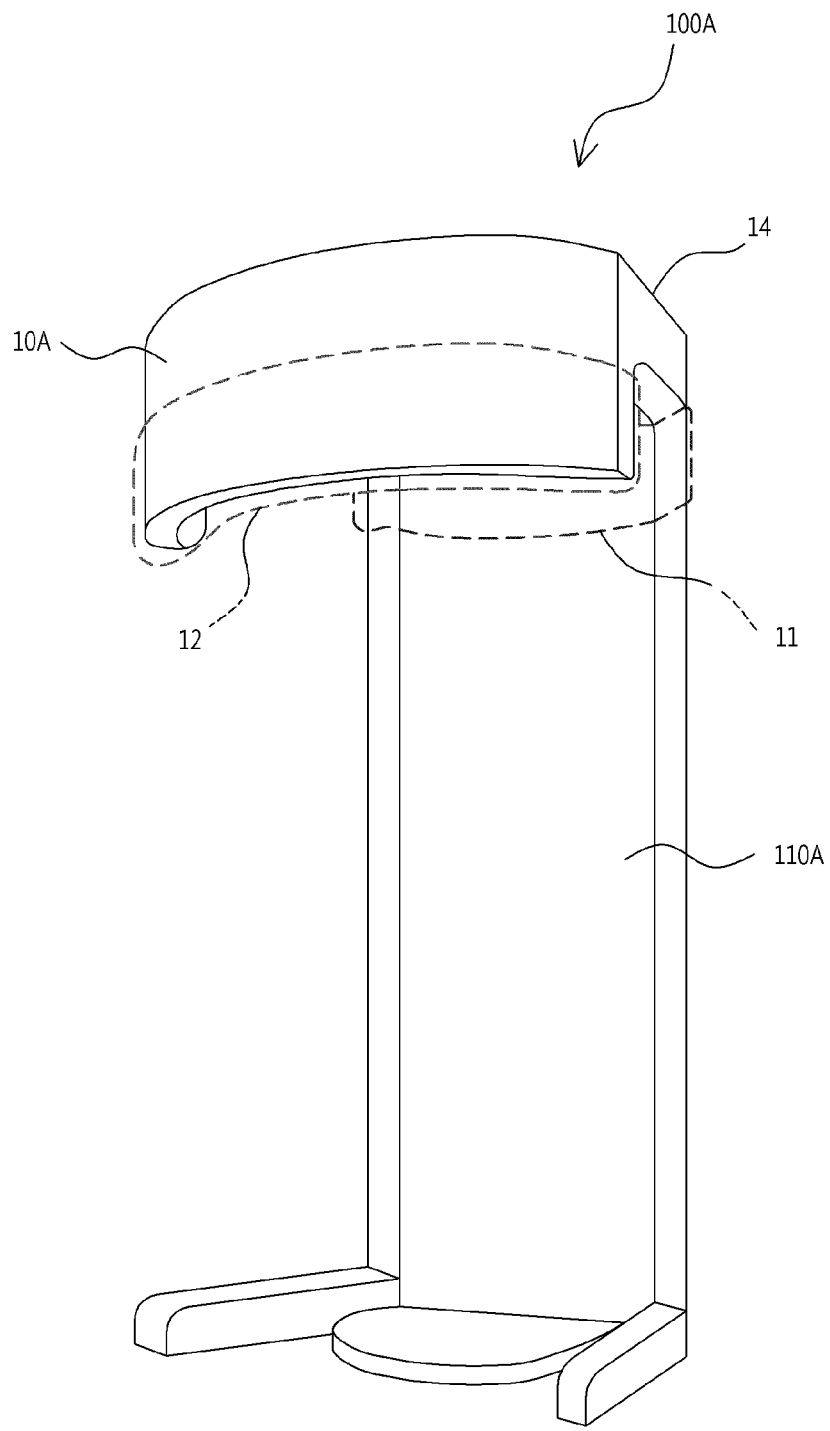
FIGS. 10 and 11 illustrate exemplary dental CT apparatuses respectively having an integrated case structure to which the CT method according to the present invention is applied.
Figure 11:
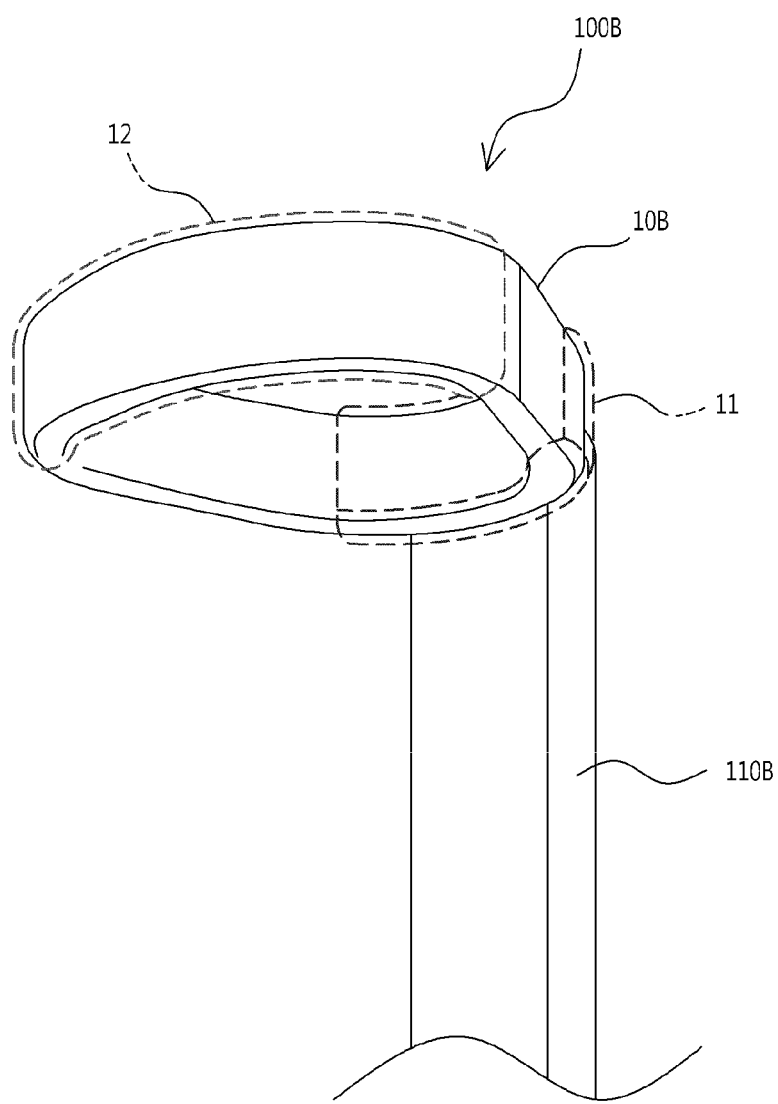

FIG. 10 and FIG. 11 illustrate exemplary dental CT apparatuses respectively having an integrated case structure to which the CT method according to the present invention is applied.

The integrated case 10A of the CT apparatus 100A according to the embodiment illustrated in FIG. 10 is disposed on the prop 110A supporting the CT apparatus in a position of being vertically erected on the floor. In a position in which a patient is standing in front of the prop 110A, the first area 11 that is closer to the subject and has a smaller radius of curvature may be disposed behind the head of the patient, and the second area 12 that is farther from the subject and has a greater radius of curvature may be disposed in front of the head of the patient. For some purposes, the opposite configuration is possible. The first area 11 and the second area are connected via a ceiling area 14. In this case, as in the embodiment illustrated in FIG. 5, the rotary arm may be disposed within the ceiling area 14. However, this is not intended to be limiting. As in the embodiment illustrated in FIG. 6, the tracks may be disposed within the first area 11 and the second area 12.

The CT apparatus 100B according to the embodiment illustrated in FIG. 11 includes the integrated case 10B, the ceiling area of which has the shape of an open rim. Although the prop 110B which is vertically supporting the CT apparatus is engaged with the portion corresponding to the first area 11, the prop 110B may be engaged with the portion corresponding to the second area 12. When the rim-shaped integrated case 10B is provided as in the CT apparatus 100B according to the present embodiment, it is preferable that the inner configuration of the integrated case 10B corresponds to that of the embodiment described above with reference to FIG. 6.

Figure 12:
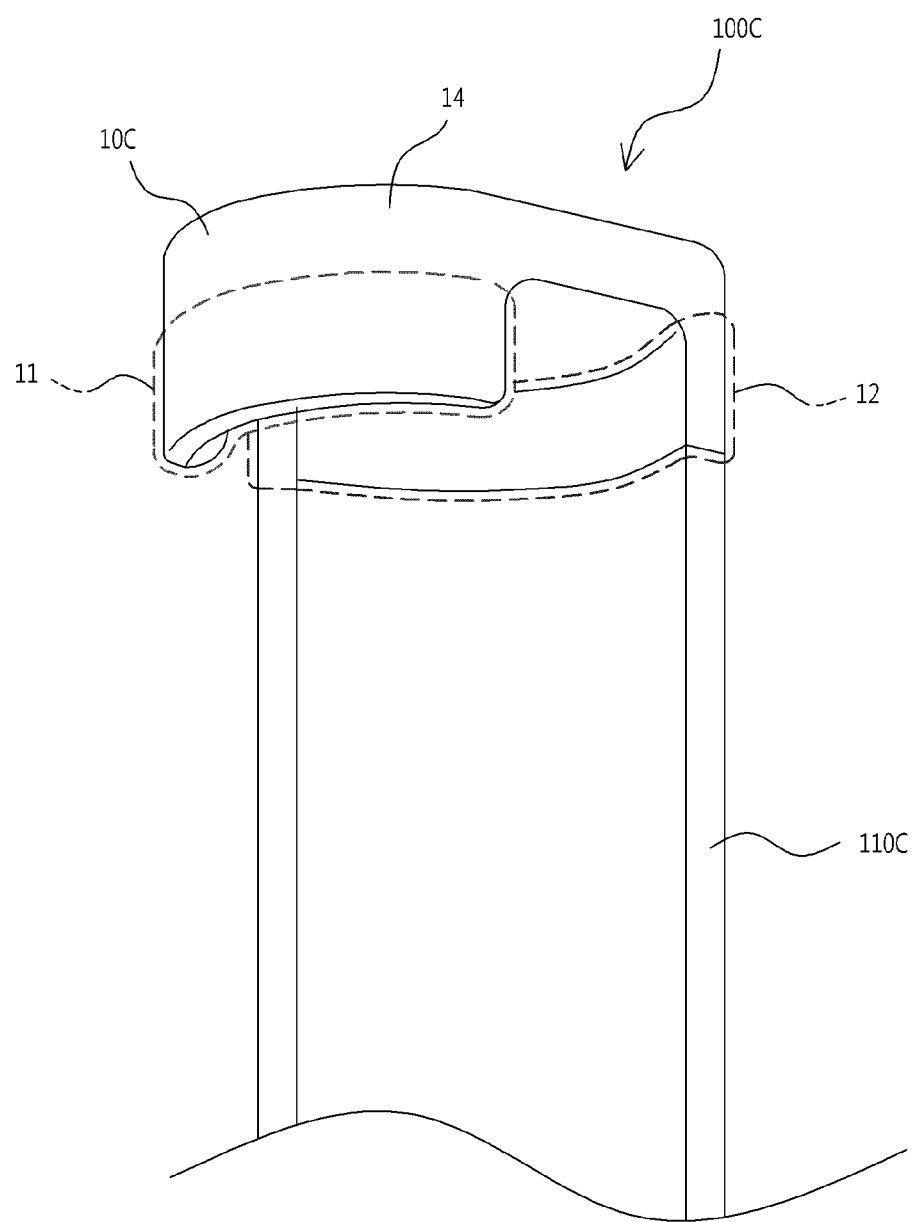
FIG. 12 illustrates the configuration of an integrated case of a CT apparatus according to an embodiment of the present invention.

FIG. 12 illustrates the configuration of an integrated case of a CT apparatus according to an embodiment of the present invention. The integrated case 10C of the CT apparatus 100C according to the present embodiment is similar to that of the embodiment illustrated in FIG. 3. In contrast, the CT apparatus 100C differs from the embodiment illustrated in FIG. 3, in that the distance of the prop 110C to the subject is greater, and that the prop 110C is disposed to be connected to the second area 12 having a greater radius of curvature.

Figure 13:
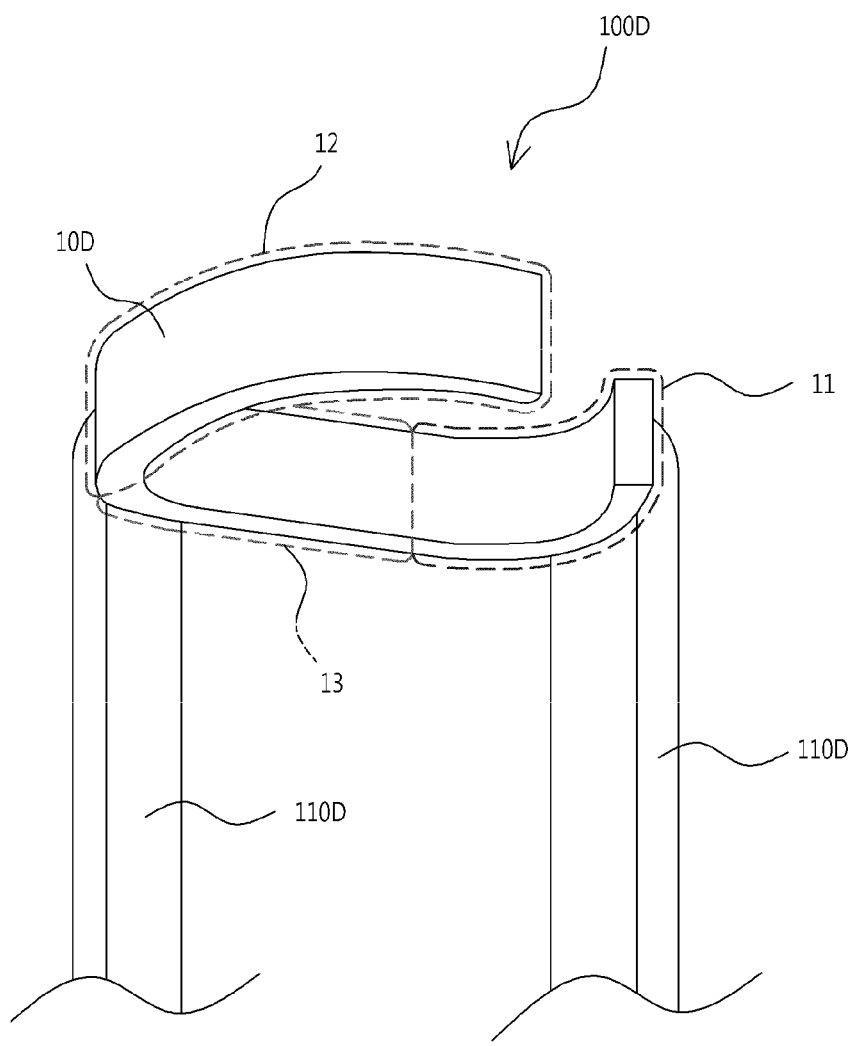
FIG. 13 illustrates the configuration of an integrated case of a CT apparatus according to an embodiment of the present invention.

FIG. 13 illustrates the configuration of an integrated case of a CT apparatus according to an embodiment of the present invention. In the CT apparatus according to the present embodiment 100D, the integrated case 10D has the shape of an asymmetric letter "C", in which the third area 13 connecting the first area 11 and the second area 12 along extensions thereof is formed only on one side. As discussed with respect to the embodiment illustrated in FIG. 1, no structure is disposed within the third area 13 of the integrated case 13. Thus, when only the rigidity of the integrated case and supporting force using the prop 110D are obtained, it is possible to realize the integrated case 10D in which one side thereof in addition to the ceiling area is open.

Figure 14:
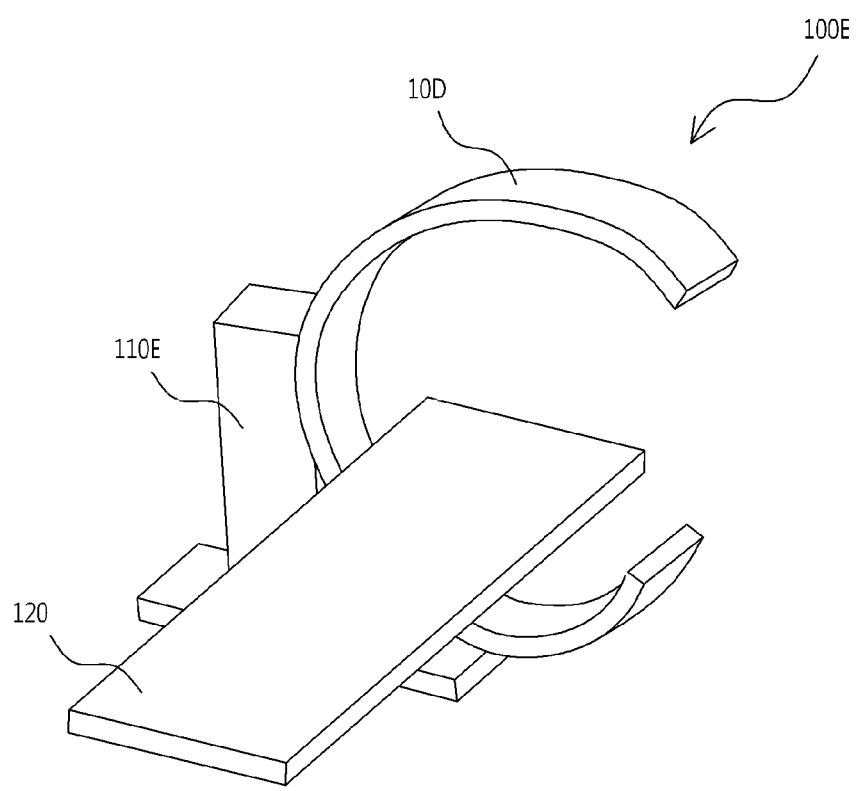
FIG. 14 illustrates another embodiment in which the integrated case of the CT apparatus according to the embodiment illustrated in FIG. 13 is vertically erected.

FIG. 14 illustrates an application in which the integrated case of the CT apparatus according to the embodiment illustrated in FIG. 13 is vertically erected. As illustrated in this drawing, the integrated case 10D having the shape of asymmetric C according to the embodiment illustrated in FIG. 13 is vertically erected on the floor, and the prop 110E supporting the integrated case is disposed. This configuration may provide the CT apparatus 100E able to obtain images from a patient lying on a bed 120. When this apparatus 100E or the bed 120 is configured as a mobile structure, the structure such as the bed 120 can pass through the open part having the shape of asymmetric C.

Although not illustrated in the drawing, the angle of the integrated case 10D having the shape of asymmetric C may be set to be adjustable depending on the angle of the backrest of a dental chair, such that the integrated case 10D can be used together with the chair.

A CT method according to an embodiment of the present invention includes: a first driving step of driving the X-ray sensor and the X-ray generator disposed on both sides of a subject and facing each other to reciprocally rotate around the subject in the range of a predetermined angle; and a second driving step of driving the X-ray sensor and the X-ray generator, simultaneously or alternately with the first driving step, to control the X-ray sensor and the X-ray generator to move in the vertical direction of the subject. Here, the first driving step and the second driving step may be simultaneously performed, whereby the X-ray sensor and the X-ray generator form Z-shaped paths. Alternatively, the first driving step and the second driving step may be alternately performed, whereby the X-ray sensor and the X-ray generator form vertically-mirrored S-shaped paths.

In the variety of embodiments as described above, the CT method can be realized according to the operation sequences of the controller controlling the components corresponding to the first driving unit and the second driving unit. Detailed features are the same as the operations of the foregoing embodiments as described above.

The invention claimed is:

1. A computed tomography apparatus comprising:
an X-ray sensor and an X-ray generator disposed on both sides of a subject and facing each other;
a first driving unit configured to move at least one of the X-ray sensor and the X-ray generator reciprocally in an angle range;
a second driving unit configured to move at least one of the X-ray sensor and the X-ray generator in a vertical direction of the object, simultaneously or alternately with the first driving unit, whereby the first driving unit and the second driving unit provide an X-ray sensor movement and/or an X-ray generator movement;
an integrated case including a first area covering the X-ray sensor movement and a second area covering the X-ray generator movement;
a first track configured to slidably guide the X-ray generator within the first area;
a second track configured to slidably guide the X-ray sensor within the second area; and
a track lift configured to move at least one of the first track and the second track by the second driving unit in a different direction than the first track and the second track.

2. The computed tomography apparatus according to claim 1, wherein the second driving unit configured to move at least one of the X-ray sensor and the X-ray generator, simultaneously with an operation of the first driving unit, to form a Z-shaped path, or configured to move at least one of the X-ray sensor and the X-ray generator, alternately with the operation of the first driving unit, to form a vertically-mirrored S-shaped path.

3. The computed tomography apparatus according to claim 1, wherein the angle ranges from 30° to 180°, and the reciprocal movement is a rectilinear or rotational movement.

4. The computed tomography apparatus according to claim 1, wherein the first area covers the angle range of 0° or from 30° to 180°, and the second area covers angle range of 30° to 180°.

5. The computed tomography apparatus according to claim 1, further comprising a rotary arm configured to mount the X-ray sensor and the X-ray generator,
wherein the integrated case further includes a ceiling area connecting the first area and the second area and covering the rotary arm.

6. The computed tomography apparatus according to claim 1, wherein the integrated case further includes a third area connecting the first area and the second area.

7. The computed tomography apparatus according to claim 1, wherein the first area having a first radius of curvature and the second area having a second radius of curvature different from the first radius of curvature.

8. The computed tomography apparatus according to claim 1, wherein the track lift includes:
a first track lift configured to move the first track; and
a second track lift configured to move the second track.

9. The computed tomography apparatus according to claim 1, wherein the track lift configured to define the angle range at the first track and the second track.

10. The computed tomography apparatus according to claim 1, wherein the first track is shorter than the second track.

11. A computed tomography method by a computed tomography apparatus comprising an X-ray sensor, an X-ray generator, an integrated case, a first track, a second track, and a track lift, the computed tomography method comprising:
a first driving step to move reciprocally at least one of the X-ray sensor and the X-ray generator, disposed on both sides of a subject and facing each other, in an angle range; and
a second driving step to move at least one of the X-ray sensor and the X-ray generator, simultaneously or alternately with the first driving step, to control the at least one of the X-ray sensor and the X-ray generator to move in a vertical direction of the subject,
wherein the first driving step and the second driving step performs an X-ray sensor movement and an X-ray generator movement within the integrated case including a first area covering the X-ray sensor movement and a second area covering the X-ray generator movement, and
wherein the first driving step and the second driving step comprises:
slidably guiding the X-ray generator along the first track within the first area;
slidably guiding the X-ray sensor along the second track within the second area; and
moving at least one of the first track and the second track along the track lift by the second driving unit in a different direction than the first track and the second track.

12. The computed tomography method according to claim 11, wherein the second driving step includes driving at least one of the X-ray sensor and the X-ray generator, simultaneously with the first driving step, to form a Z-shaped path, or alternately with the first driving step, to form a vertically-mirrored S-shaped path.

13. The computed tomography method according to claim 11, wherein the angle in the first driving step ranges from 30° to 180°, and the reciprocal movement is a rectilinear or rotational movement.

* * * * *